(12) United States Patent
Biedermann et al.

(10) Patent No.: US 9,655,652 B2
(45) Date of Patent: May 23, 2017

(54) BONE ANCHORING DEVICE

(75) Inventors: Lutz Biedermann, VS-Villingen (DE); Wilfried Matthis, Weisweil (DE); Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 548 days.

(21) Appl. No.: 11/895,364

(22) Filed: Aug. 24, 2007

(65) Prior Publication Data
US 2008/0086132 A1 Apr. 10, 2008

Related U.S. Application Data

(60) Provisional application No. 60/840,099, filed on Aug. 24, 2006.

(30) Foreign Application Priority Data

Aug. 24, 2006 (EP) ..................................... 06017651

(51) Int. Cl.
*A61B 17/70* (2006.01)

(52) U.S. Cl.
CPC ...... *A61B 17/7032* (2013.01); *A61B 17/7037* (2013.01); *A61B 17/7026* (2013.01)

(58) Field of Classification Search
CPC . A61B 17/70; A61B 17/7001; A61B 17/7032; A61B 17/7034; A61B 17/7035;
(Continued)

(56) References Cited

U.S. PATENT DOCUMENTS

| 5,385,583 A | 1/1995 | Cotrel |
| 5,443,467 A | 8/1995 | Biedermann et al. |

(Continued)

FOREIGN PATENT DOCUMENTS

| AU | B-20478/92 | 2/1993 |
| EP | 0 528 706 A1 | 8/1991 |

(Continued)

OTHER PUBLICATIONS

European search report dated Feb. 1, 2007 for EPO Application No. 06017651.8, European Search Report mailed Feb. 13, 2007; Biedermann Motech GmbH (6 pp.).

(Continued)

*Primary Examiner* — Lynnsy Summitt
(74) *Attorney, Agent, or Firm* — Lewis Roca Rothgerber Christie LLP

(57) ABSTRACT

A bone anchoring device includes an anchoring element having a shank to be anchored in a bone or a vertebra and a receiving part connected to the shank, and a rod for connecting at least two anchoring elements, the rod having at least a tubular portion. The receiving part comprises a recess for receiving said rod. The bone anchoring element also includes a locking element cooperating with the receiving part to secure the rod in the recess, a filling piece being arranged between the locking element and the rod for exerting pressure onto the rod to lock the rod in the recess. The filling piece includes a rod contacting surface which contacts a portion of said rod. The shape of the rod contacting surface is adapted to the shape of the portion of the rod.

16 Claims, 7 Drawing Sheets

(58) Field of Classification Search
CPC .............. A61B 17/7037; A61B 17/704; A61B 18/7041; A61B 17/7043; A61B 17/7046
USPC ................................ 606/103, 151, 246–279
See application file for complete search history.

(56) References Cited

U.S. PATENT DOCUMENTS

| | | | | |
|---|---|---|---|---|
| 5,520,689 | A * | 5/1996 | Schlapfer | A61B 17/701 606/270 |
| 6,565,565 | B1 * | 5/2003 | Yuan et al. | 606/272 |
| 6,835,196 | B2 * | 12/2004 | Biedermann | A61B 17/7032 606/308 |
| 6,896,677 | B1 * | 5/2005 | Lin | 606/266 |
| 7,625,394 | B2 * | 12/2009 | Molz, IV | A61B 17/7037 606/270 |
| 7,722,651 | B2 * | 5/2010 | Kwak | A61B 17/7032 606/246 |
| 7,731,749 | B2 | 6/2010 | Biedermann et al. | |
| 7,766,915 | B2 * | 8/2010 | Jackson | A61B 17/7028 606/254 |
| 7,780,706 | B2 * | 8/2010 | Marino | A61B 17/7037 606/264 |
| 7,794,481 | B2 * | 9/2010 | Molz, IV | A61B 17/7037 606/270 |
| 7,914,559 | B2 * | 3/2011 | Carls | A61B 17/7032 606/270 |
| 7,967,850 | B2 * | 6/2011 | Jackson | A61B 17/7032 606/301 |
| 8,157,843 | B2 | 4/2012 | Biedermann et al. | |
| 8,282,672 | B2 | 10/2012 | Freudiger | |
| 2002/0143341 | A1 * | 10/2002 | Biedermann et al. | 606/73 |
| 2003/0100896 | A1 * | 5/2003 | Biedermann | A61B 17/7032 606/305 |
| 2003/0100904 | A1 * | 5/2003 | Biedermann | A61B 17/7032 606/272 |
| 2003/0125741 | A1 * | 7/2003 | Biedermann et al. | 606/61 |
| 2003/0187434 | A1 * | 10/2003 | Lin | 606/61 |
| 2004/0049190 | A1 * | 3/2004 | Biedermann | A61B 17/7008 606/257 |
| 2004/0138660 | A1 | 7/2004 | Serhan | |
| 2004/0260283 | A1 * | 12/2004 | Wu | A61B 17/7032 606/270 |
| 2004/0260284 | A1 * | 12/2004 | Parker | A61B 17/7032 606/276 |
| 2005/0055026 | A1 * | 3/2005 | Biedermann | A61B 17/1659 606/278 |
| 2005/0085815 | A1 * | 4/2005 | Harms | A61B 17/645 606/279 |
| 2005/0131410 | A1 * | 6/2005 | Lin | A61B 17/7037 606/266 |
| 2005/0154390 | A1 | 7/2005 | Biedermann et al. | |
| 2005/0187548 | A1 * | 8/2005 | Butler | A61B 17/7032 606/278 |
| 2005/0203517 | A1 | 9/2005 | Jahng et al. | |
| 2005/0240180 | A1 * | 10/2005 | Vienney | A61B 17/7032 606/246 |
| 2005/0261687 | A1 * | 11/2005 | Garamszegi | A61B 17/7011 606/305 |
| 2005/0283244 | A1 * | 12/2005 | Gordon | A61B 17/7005 623/17.15 |
| 2006/0036244 | A1 * | 2/2006 | Spitler | A61B 5/103 74/1 R |
| 2006/0241595 | A1 * | 10/2006 | Molz, IV | A61B 17/7038 606/278 |
| 2007/0049937 | A1 | 3/2007 | Matthis et al. | |
| 2007/0055244 | A1 * | 3/2007 | Jackson | A61B 17/7028 606/86 A |
| 2007/0161999 | A1 * | 7/2007 | Biedermann | A61B 17/7037 606/254 |
| 2007/0270832 | A1 * | 11/2007 | Moore | A61B 17/7011 606/278 |
| 2007/0288002 | A1 * | 12/2007 | Carls | A61B 17/7032 606/86 A |
| 2008/0161863 | A1 * | 7/2008 | Arnold | A61B 17/7004 606/319 |
| 2010/0069962 | A1 | 3/2010 | Harms et al. | |
| 2011/0040335 | A1 * | 2/2011 | Stihl | A61B 17/7032 606/302 |

FOREIGN PATENT DOCUMENTS

| | | |
|---|---|---|
| EP | 0 528 706 A1 | 2/1993 |
| EP | 1 604 617 A1 | 12/2005 |
| FR | 2 810 533 | 6/2000 |
| FR | 2 829 014 | 9/2001 |
| JP | 2005-253971 A | 9/2005 |
| JP | 2007-502692 A | 2/2007 |
| JP | 2007-54628 A | 3/2007 |
| TW | 239290 | 1/1995 |
| TW | 257967 | 9/1995 |
| WO | WO 98/27884 | 7/1998 |
| WO | WO 2004/105577 A2 | 12/2004 |
| WO | WO 2006/071742 A2 | 7/2006 |
| WO | WO 2006116437 A2 * | 11/2006 |

OTHER PUBLICATIONS

English translation of Office action for EP priority application No. 06 017 651.8, issued Feb. 2, 2013, 2 pages.
English translation of Office action for parallel TW Application No. 096130811, dated Jan. 31, 2013, 4 pages.

* cited by examiner

US 9,655,652 B2

BONE ANCHORING DEVICE

RELATED APPLICATIONS

The present application claims the benefit of U.S. Provisional Patent Application Ser. No. 60/840,099, filed Aug. 24, 2006, and claims priority from European Patent Application Number EP06017651.8, filed Aug. 24, 2006.

BACKGROUND

The application relates to a bone anchoring device having a bone anchoring element and a rod for connecting at least two bone anchoring elements wherein the rod has at least in a part thereof a tubular structure.

FIG. 12 shows a known polyaxial bone screw 100 with a screw element 101 having a bone thread and a spherical segment-shaped head 102 which is pivotably held in a receiving part 103. The receiving part has a recess for receiving a rod 104. Between the head 102 and the rod a pressure element 105 is provided which is slidable in the receiving part. An inner screw 106 is used to clamp the rod in the receiving part and to exert pressure onto the head via the rod and the pressure element to lock the head. A flexible rod having a tubular structure for stabilizing the spine is known for example from US 2005/0154390 A1. When a tubular rod is used together with the known polyaxial bone screw as described with reference to FIG. 12, the load which acts on the rod when the inner screw is tightened can deform the tubular rod as shown schematically in FIG. 13. This will affect the properties of the rod.

US 2004/0138660 A1 discloses a locking cap assembly for locking a rod which is made from a full metal cylinder to a receiving body of a bone screw. The locking cap assembly includes an inner and an outer locking element. The outer locking element is a nut-like member to which the inner locking element is rotatably connected. The inner locking element has on its side facing the rod a ring-shaped deformable contacting element which comes into contact with the rod. Upon tightening of the outer locking element, the deformable contacting element is deformed which provides feed-back to the surgeon to allow him to determine whether the locking cap assembly is tightened to the required extent.

FR 2 810 533 discloses a bone anchoring device with a rod which is made from a full cylinder. A locking cap assembly comprises a rotatably supported member which presses from above onto the rod. The shape of the rod contacting surface of said member is adapted to the contour of the rod.

Based on the above, there is a need to provide a bone anchoring device which is suitable for a dynamic stabilization and which comprises an improved fixation of the tubular portion of a rod.

SUMMARY

A bone anchoring device according to the disclosure provides a fixation of a tubular rod wherein a deformation of the tubular rod is minimized even in the case when a large clamping force is exerted.

Further features and advantages of the invention will become apparent and will be best understood by reference to the following detailed description of embodiments taken in conjunction with the accompanying drawings.

DETAILED DESCRIPTION

Figure 1:
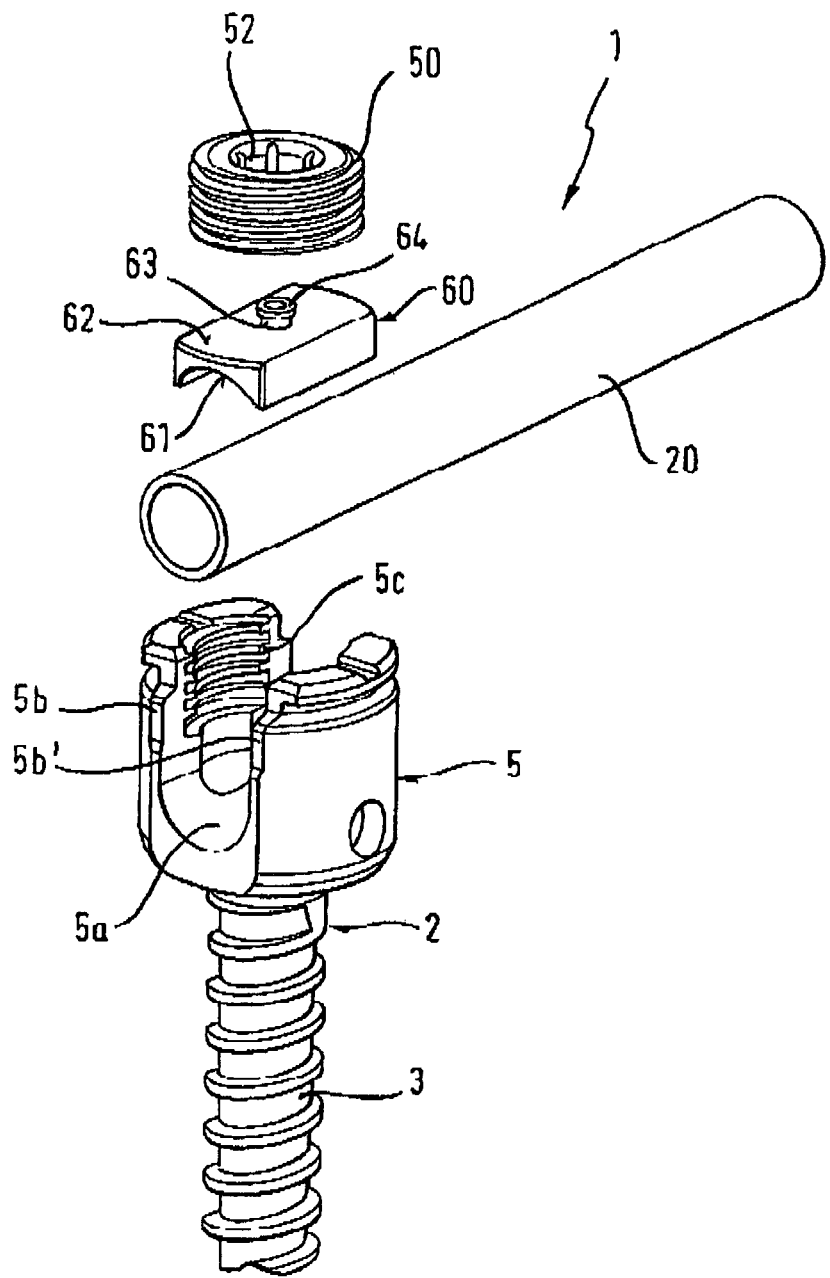
FIG. 1 shows an exploded view of the bone anchoring device according to a first embodiment.
Figure 2:
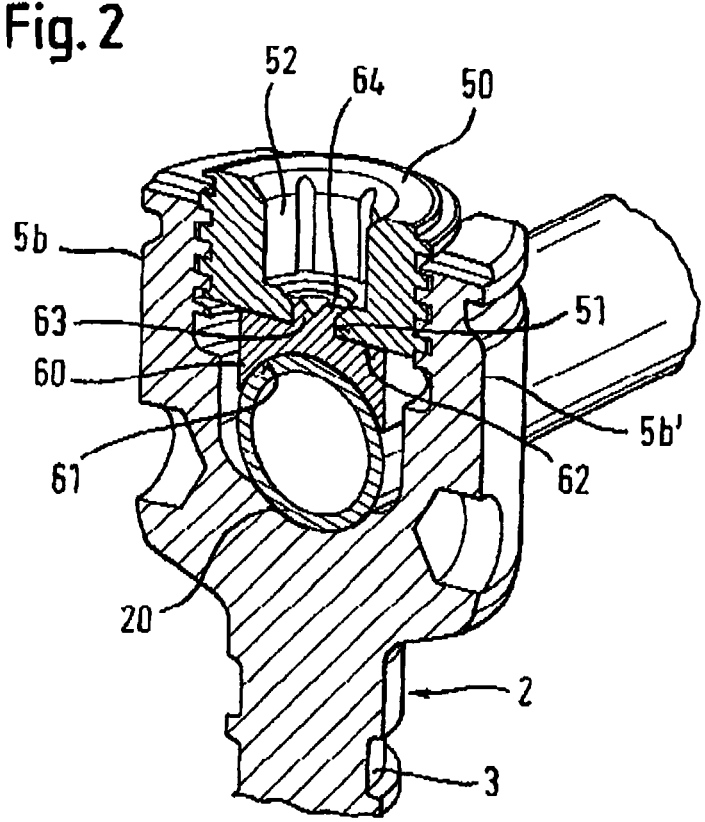
FIG. 2 shows a perspective sectional view of the bone anchoring device according to FIG. 1 in an assembled and fixed state.

FIGS. 1 and 2 show a bone anchoring device 1 according to a first embodiment. The bone anchoring device 1 includes a monoaxial bone screw 2 and a tubular rod 20. The bone screw 2 has a shank 3 with a bone thread for anchoring in the bone, a tip at one end (not shown) and a receiving part 5 at the opposite end. The receiving part 5 comprises a substantially U-shaped recess 5a for receiving the rod 20. By means of the recess, two free legs 5b, 5b' are formed which have an internal thread 5c for receiving a locking element to secure the rod 20 in the recess. In the embodiment shown, the locking element is an inner screw 50 which can be screwed-in between the legs. The thread can be a flat thread to prevent splaying of the legs when tightening the inner screw. However, any other thread shape such as a metric thread, a saw tooth thread or a negative angle thread can be used. In the assembled state, the rod 20 rests on the bottom of the recess 5a.

Between the inner screw 50 and the rod a filling piece 60 is provided. The outer contour of the filling piece 60 when viewed from above is substantially rectangular with two opposite long straight sides and two opposite outwardly curved short sides. On its side facing the rod the filling piece has a rod contacting surface 61 the shape of which is adapted to the shape of the rod surface. In the embodiment shown, the rod 20 is cylindrically-shaped. Hence, the rod contacting surface 61 is formed by a cylinder segment-shaped recess in the filling piece. The size of the rod contacting surface 61 is selected so as to provide a desired load distribution when the rod is clamped between the filling piece and the bottom of the U-shaped recess 4a. The surface 62 opposite to the rod contacting surface 61 is substantially flat with a cylindrical projection 63 in the center. The cylindrical projection 63 is insertable in a corresponding cylindrical bore 51 of the inner screw 50 provided at the underside of the inner screw. By means of this, the inner screw is rotatable with respect to the filling piece. At its free end, the projection 63 can have an outwardly projecting rim 64 cooperating with a corresponding circular recess in the inner screw so that the filling piece is rotatably supported in the inner screw. The inner screw further has a recess 52 on the opposite side for engagement with a tool.

The rod 20 is formed as a cylindrical tube.

All parts of the bone anchoring device are made of a biocompatible material, for example of a metal such as titanium or a metal alloy or a biocompatible plastic material.

Figure 3A:
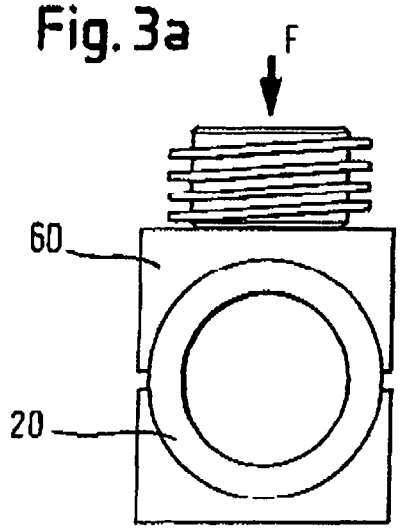
FIGS. 3a and 3b schematically show the clamping of the rod under the action of a smaller and a larger clamping force F.
Figure 3B:
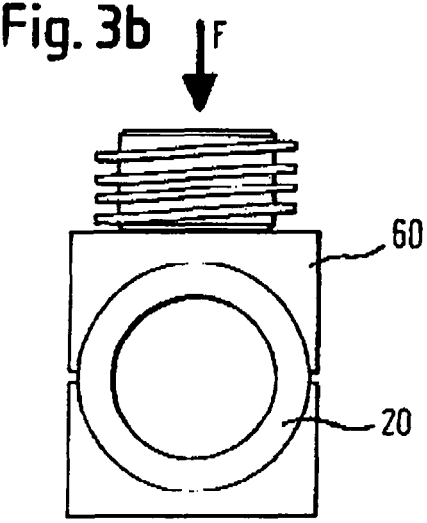

In use at least two bone anchoring elements are anchored into two vertebrae or two bone parts which are to be stabilized with the rod. Thereafter the rod is inserted into the receiving parts. Then the inner screw with the filling piece is inserted and the inner screw is tightened. As can be seen in FIGS. 3a and 3b a deformation of the tubular rod is minimized or does even not occur when the filling piece presses with its rod contacting surface 61 against the surface of the rod. The homogeneous load distribution on the surface of the rod prevents a deformation of the rod.

Figure 4:
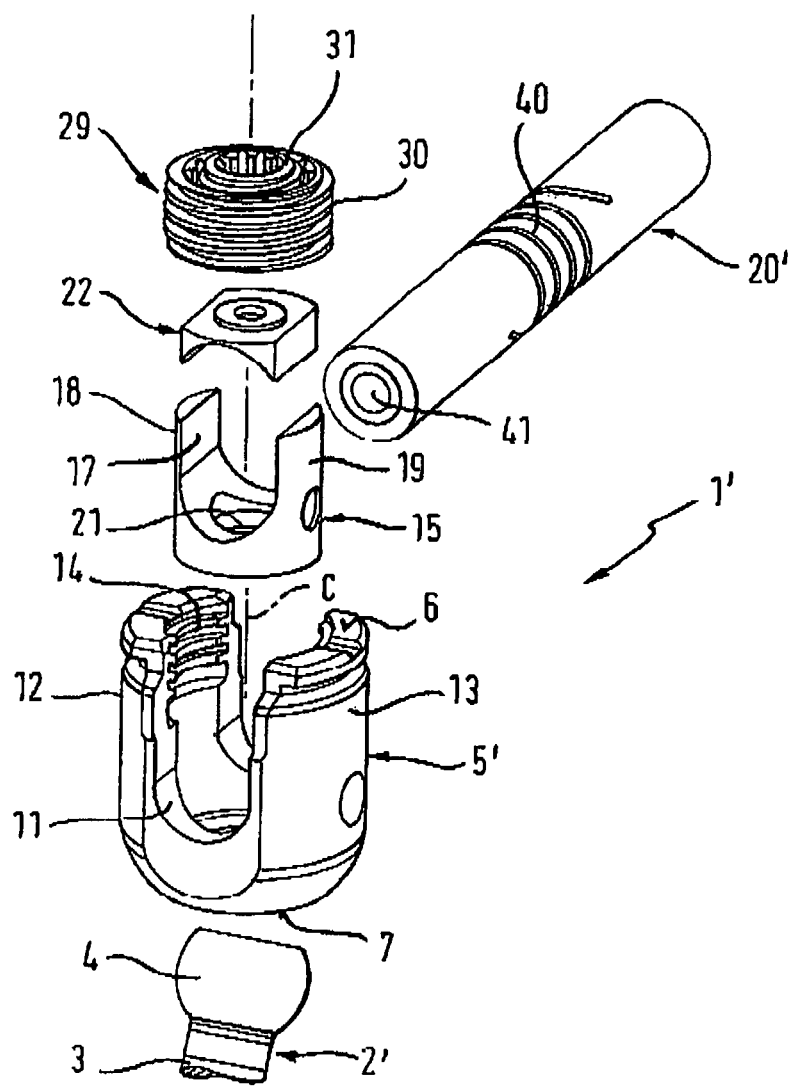
FIG. 4 shows an exploded view of the bone anchoring device according to a second embodiment.
Figure 5:
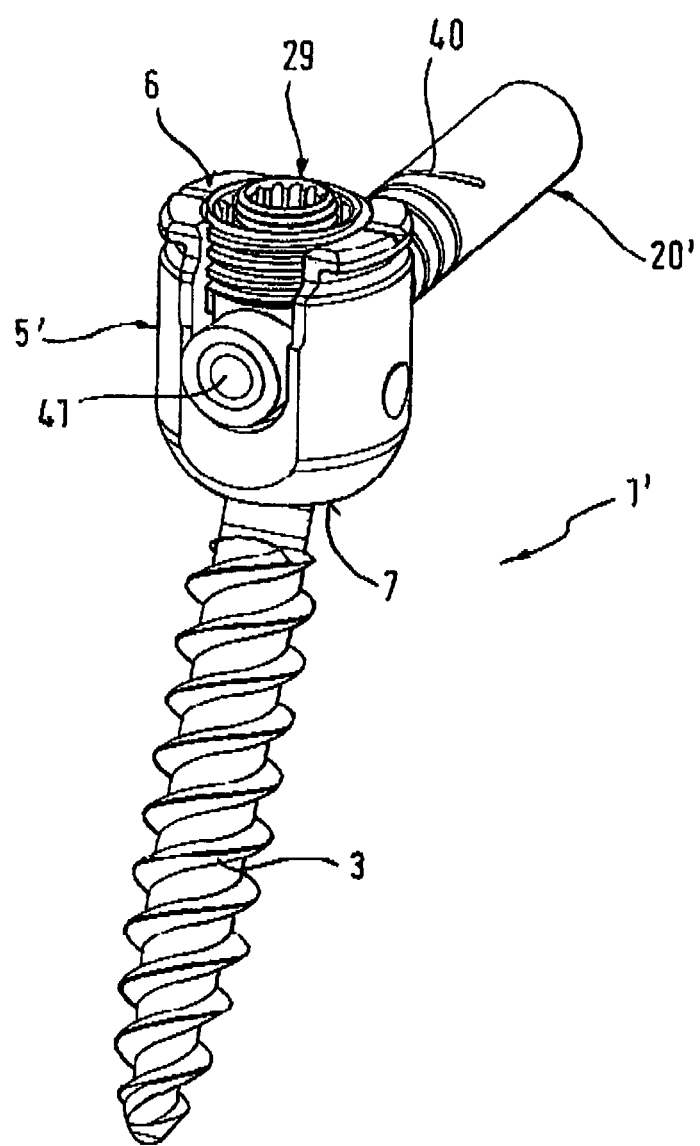
FIG. 5 shows a perspective view of the bone anchoring device of FIG. 4 in an assembled state.
Figure 6:
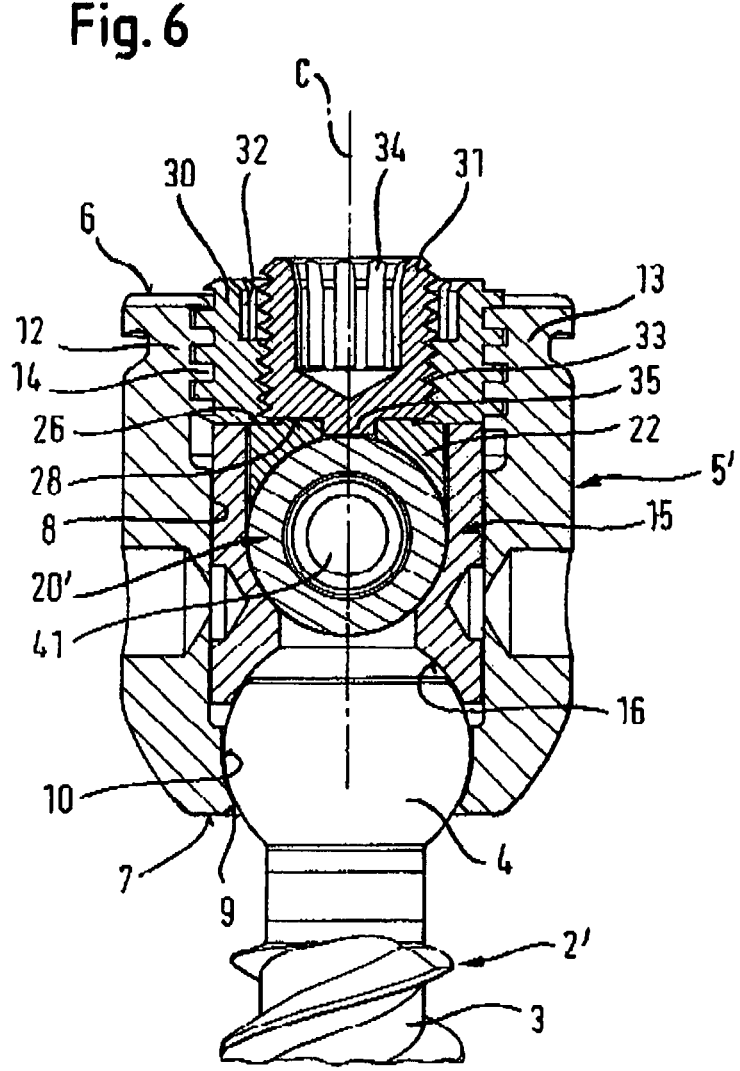
FIG. 6 shows a sectional view of the bone anchoring device in an assembled and fixed state as shown in FIG. 4.
Figure 7:
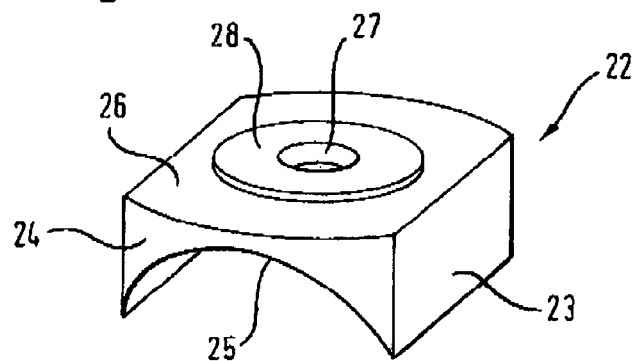
FIG. 7 shows a perspective view of a filling piece which is part of the bone anchoring device of FIG. 4.
Figure 8:
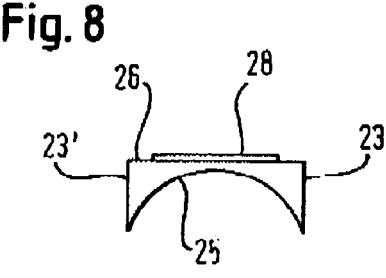
FIG. 8 shows a side view of the filling piece of FIG. 7 in the direction of the rod axis.
Figure 9:
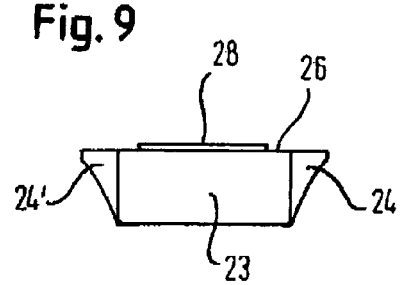
FIG. 9 shows a side view of the filling piece of FIG. 7 rotated by 90°.
Figure 10:
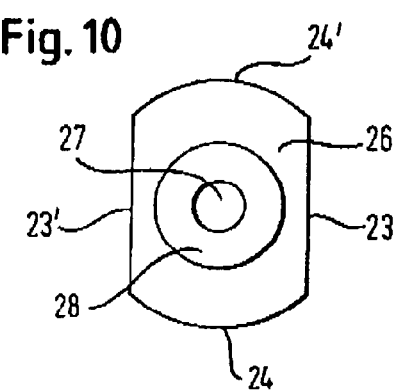
FIG. 10 shows a top view of the filling piece of FIG. 7.
Figure 11:
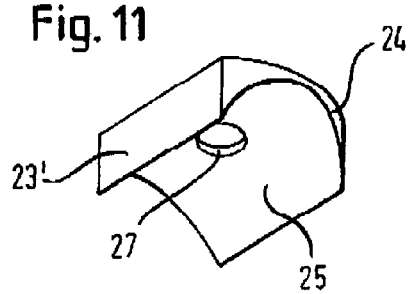
FIG. 11 shows a perspective view of the filling piece of FIG. 7 from the bottom.
Figure 12:
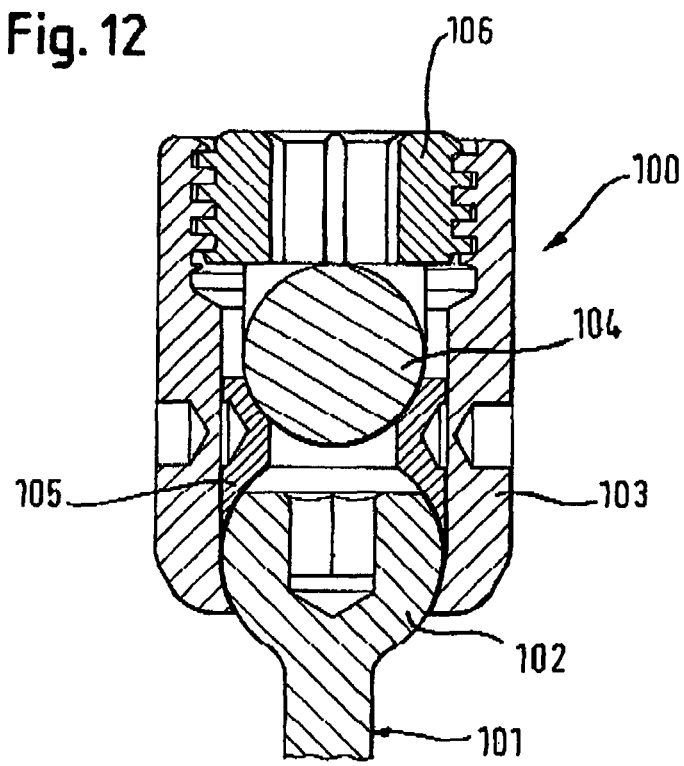
FIG. 12 shows a schematic cross-sectional view of a prior art polyaxial bone screw with a rod.
Figure 13:
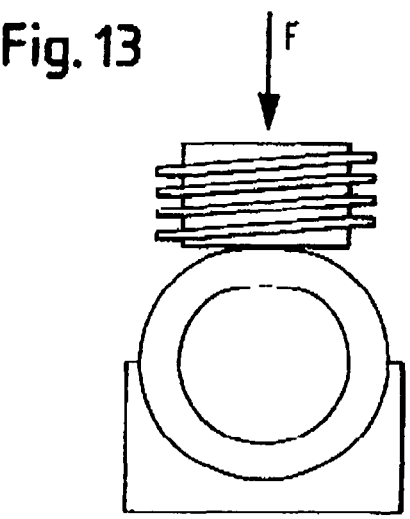
FIG. 13 shows a schematic view of the rod clamping in the case of using the polyaxial screw of FIG. 12 with a tubular rod.

As shown in FIGS. 4 and 6, the bone anchoring device 1' according to a second embodiment is of the polyaxial type and includes a bone anchoring element 2' in the form of a bone screw having a shank 3 with a bone thread and a tip (not shown) and a head 4. In the example shown, the head 4 has a spherical segment shape. A recess (not shown) for the engagement with a screwing-in tool is provided at the free end of the head 4.

The bone anchoring device further comprises a receiving part 5' which has a first end 6 and an opposite second end 7, a central axis C going through the planes defined by the first end and the second end, respectively, and a coaxial bore 8 extending from the first end to a distance from the second end. At the second end 7 an opening 9 is provided the diameter of which is smaller than the diameter of the bore 8. A spherically shaped section 10 is provided adjacent to the opening 9 which forms a seat for the head 4. The section which forms the seat can have other shapes, for example, a conical shape.

The receiving part 5' has a substantially U-shaped recess 11 which starts at the first end 6 and extends to a distance from the second end 7 for receiving the rod 20'. By means of the U-shaped recess 11 two free legs 12, 13 are formed. In addition, the receiving part 5' further comprises an internal thread 14 on the legs 12, 13.

The bone anchoring device 1 further comprises a pressure element 15. In the embodiment shown the pressure element 15 has a substantially cylindrical construction with an outer diameter which is only slightly smaller than the inner diameter of the bore 8 to allow the pressure element 15 to be introduced into the bore 8 and to be moved in the axial direction. On its lower side facing towards the second end 7 the pressure element 15 comprises a spherical recess 16 the radius of which corresponds substantially to the radius of the head 4 of the bone screw. On the opposite side a substantially U-shaped recess 17 is provided the depth of which is larger than the diameter of a rod 20. The rod 20 connects at least two bone screws. By means of the U-shaped recess 17 two free legs 18, 19 are provided, which extend above the surface of the rod 20 when the rod is seated in the pressure element 15. The pressure element 15 further comprises a coaxial bore 21 for allowing access with a screwing-in tool to the screw head 4.

The bone anchoring device further comprises a filling piece 22 which is depicted in more detail in FIGS. 7 to 11. In the embodiment shown, the filling piece is sized so as to be slidable in the U-shaped recess 17 of the pressure element. It has two opposite flat side walls facing the inner side of the legs 18, 19 of the pressure element 15. Further, it has two opposite rounded sides 24,24'. On its lower side the filling piece 22 comprises a recess 25 for accommodating the rod 20. In the embodiment shown the rod 20 is a cylindrical rod and the recess 25 is adapted to the shape and size of the rod 20. The depth of the recess is smaller or equal to the radius of the rod 20 so that the filling piece 22 is able to exert pressure from above on the surface of the rod 20. On the opposite side of the recess 25 the filling piece 22 comprises a substantially flat surface 26. Further, it comprises a coaxial bore 27. Around the coaxial bore a contact surface 28 is provided which projects from the flat surface 26. The contact surface is, for example, ring-shaped.

The dimension of the filling piece 22 in this embodiment as shown in FIG. 4, can be such that in the assembled state when the rod 20 rests in the U-shaped recess 17 of the pressure element 15 and the filling piece 22 is placed on top of the rod, the surface 26 is located slightly below the end surface of the legs 18, 19 of the pressure element 15.

The bone anchoring device comprises a locking device 29 for fixation of the rod and of the head. In the embodiment shown, the locking device 29 consists of a first locking element 30 in form of an inner screw cooperating the internal thread 14 of the receiving part 5'. For example, as shown in FIG. 6, the cooperating threads are shaped as flat threads. However, any other thread shape is possible. The first locking element 30 comprises an engagement structure 32 for engaging a screwing-in tool and a coaxial threaded bore 33 for the reception of the second locking element 31 which is shaped as a set screw. The second locking element 31 also comprises an engagement structure 34 for engagement with a screwing-in tool. On the side facing the rod a projection 35 which is shaped so as to fit into the bore 27 of the filling piece 22 and to allow a rotational movement between the filling piece 22 and the second locking element 31 is provided.

The dimensions of the locking device 29, the pressure element 15 and the filling piece 22 are such that in an assembled state as shown in FIG. 6 the first locking element 30 contacts the upper surface of the free legs 18, 19 of the pressure element but does not contact the filling piece 22. The second locking element 31 contacts the contact surface 28 of the filing piece 22 but does not contact the pressure element. By means of this, the rotational position of the head 4 in the receiving part and the position of the rod 20 in the anchoring device can be locked separately.

The material from which the bone anchoring element is made is preferably a body compatible material, such as titanium or a titanium alloy.

The rod 20' is shaped as a tube having a helix-shaped recess 40 in at least a part of its wall. The helix-shaped recess 40 provides elasticity against axial and bending forces and in specific applications also against torsional forces. The characteristics of the helix-shaped recess 40 such as the pitch, the width of the recess, the exact shape of the helix and other parameters vary according to the desired flexible properties of the rod 20'. The rod 20' further can have a core 41 with a diameter which is smaller than the inner diameter of the tube. The core 41 can be designed to be slidable within the tube. The material from which the core 41 is made and its diameter or detailed shape is selected in such a way that the desired elastic properties of the rod 20' are achieved. For example, the core 41 may be provided for enhancing the stiffness of the flexible tubular rod 20', for example to avoid kinking.

The tubular rod 20' can be made of the same material as the bone anchoring element or from another material. For example the rod can be made from a material which exhibits an enhanced elasticity per se. Such a material may be a plastic material or a shape memory alloy having shape memory and/or superelastic properties.

In use, the bone screw 2, the receiving part 5' and the pressure element 15 can be preassembled in such a way that the head 4 is pivotably held in the receiving part 5' and the pressure element 15 is loosely held and secured against rotation in the receiving part 5'. The preassembled bone anchoring elements are screwed into adjacent vertebrae of a spinal motion segment. Thereafter, the rod 20' is inserted into the receiving part so that it rests in the pressure element and in the bottom of the U-shaped recess 11 of the receiving part. The second filling piece 22 can be loosely connected to the second locking element 31 by means of the projection 35 of the second locking element extending through the bore 27 of the filling piece. Then, the preassembled locking device 29 together with the filling piece 22 is inserted into the receiving part. The angular position of the receiving part relative to the bone screw is finally adjusted and the head 4 of the bone screw locked in this position by tightening down the first locking element 30. Since the first locking element 30 abuts with its lower surface the upper surface of the legs 18, 19 of the pressure element without touching the filling piece 22, the head can be fixed by the pressure element 15. Thereafter, the position of the rod 20 is adjusted. Finally the second locking element 31 is tightened down until it presses on the contact surface 28 of the filling piece. The frictional forces acting between the pressure element and the rod, respectively, hold the rod in place.

The homogeneous load distribution on the surface of the rod which is provided by the filling piece prevents deformation. Therefore, a core 41 which is movable within the tubular rod is not jammed by a deformation of the rod.

In a further modification the locking device comprises only one single locking element. In this case, the pressure element 15 does not have legs 8,19 which extend over the surface of the rod. The filling piece presses onto the rod and the rod presses onto the pressure element so that the head and the rod are fixed simultaneously.

Other modifications of the locking device are possible, for example, a locking element having an outer nut or a cap. The filling piece 22 is then rotatably connected with an element of the locking device. Also, the two part locking device as described above can be modified, for example the first locking element 30 can have threadless section in its coaxial bore with a diameter greater than that of the filling piece such that the first locking element 30 does not touch the surface 26 of the filling piece. In this case the filling piece can extend above the legs 18, 19.

The receiving part can be designed so as to allow the introduction of the screw element from the bottom.

The rod can be totally or partially tubular. The core can be omitted. The rod can be rigid or fully or partially flexible.

Further modifications are possible. Instead of a bone screw, a hook or nail-like anchoring element can be provided. The elements of the various embodiments described can be combined. For example, the two part locking device can also be used with a monoaxial screw.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring device comprising:
   an anchoring element comprising a shank and a head;
   a rod;
   a receiving part configured to pivotably receive the head and to receive the rod for connecting the rod to the shank, the receiving part comprising two legs defining a U-shaped recess, each leg having a free end and an internal thread comprising a plurality of thread turns formed in one-piece with the leg;
   a filling piece comprising a rod contacting surface configured to correspond with shape of and contact an outer surface of a first portion of the rod, and a second surface opposite the rod contacting surface;
   a pressure element configured to be arranged its the U-shaped recess and having a seat for receiving the rod, wherein the seat of the pressure element comprises a rod contacting surface configured to face in the direction of the filling piece for contacting a second portion of the rod, wherein a shape of the rod contacting surface of the seat is adapted to the shape of an outer surface of the second portion of the rod, the pressure element having a bore through a central portion of the rod contacting surface of the seat to expose the head of the anchoring element when the pressure element is arranged in the U-shaped recess;
   a first locking element having a central axis, a solid tubular wall around the central axis and a threaded outer surface on the solid tubular wall configured to engage with the plurality of thread turns of each leg to secure the rod in the seat, the first locking element also configured to contact the pressure element when assembled with the receiving part to secure the head relative to the receiving part; and
   a second locking element configured to couple to the first locking element and contact the filling piece to secure the rod in the seat of the pressure element, the second locking element comprising an annular surface around the central ax configured to be facing in the direction of the rod when the rod is secured in the seat;
   wherein the second surface of the filling piece is configured to contact a majority of a width of said annular surface of the second locking element when the rod is secured in the seat,
   wherein the filling piece is spaced apart from the receiving part assembled in the receiving part with the rod and the pressure element,
   wherein the filling piece further comprises two opposite outward-facing flat side surfaces extending in a direction of a longitudinal axis of the rod and facing respective opposite inward-facing portions of the pressure element when the filling piece is assembled in the receiving part with the rod and the pressure element, and
   wherein the rod contacting surface of the filling piece that is configured to contact the rod has a length from a first end to a second end, and a shape of the rod contacting surface of the filling piece from the first end to the second end corresponds to the shape of the outer surface of the rod along a corresponding length of the rod in the direction of the longitudinal axis of the rod such that the rod contacting surface of the filling piece is configured to provide a homogenous load distribution along the corresponding length of the rod.

2. The bone anchoring device of claim 1, wherein the second locking element comprises a bore configured to receive a pin of the filling piece.

3. The bone anchoring device of claim 1, wherein the filling piece comprises a bore for receiving a pin of the second locking element.

4. The bone anchoring device of claim 1, wherein the rod is a hollow rod comprising a solid tube portion, and the receiving part is configured to receive the solid tube portion.

5. The bone anchoring device of claim 4, wherein the rod comprises a core in the solid tube portion.

6. The bone anchoring device of claim 4, wherein the rod comprises the solid tube portion and a portion having a helix-shaped recess, and wherein the pressure element and the filling piece are configured to contact the solid tube portion of the rod.

7. The bone anchoring device of claim 1, wherein when the pressure element, the rod and the filling piece are assembled with the receiving part, the recess of the pressure element and the rod contacting surface of the filling piece contact substantially an entire outer surface of a section of the rod located in the recess of the pressure element between the pressure element and the filling piece.

8. The bone anchoring device of claim 1, wherein at least a portion of the filling piece is located inside the recess of the pressure element.

9. The bone anchoring device of claim 1, wherein a diameter of the rod is greater than or equal to a width of the filling piece along direction perpendicular to a longitudinal axis of the receiving part when the filling piece is assembled in the receiving part.

10. The bone anchoring device of claim 1, wherein the second looking element has an outer diameter that is less than an outer diameter of the rod.

11. The bone anchoring device of claim 1, wherein the annular surface is arranged perpendicular to the central axis.

12. The bone anchoring device of claim 1, wherein an outer contour of the filling piece when viewed in a direction of the central axis is substantially rectangular having two opposite long sides and two opposite short sides.

13. The bone anchoring device of claim 1, wherein the filling piece further comprises two opposite outward-facing rounded sides spaced apart from each other in the direction of the longitudinal axis of the rod when the filling piece is assembled in the receiving part with the rod and the pressure element.

14. A bone anchoring device comprising:
an anchoring element comprising a shank and a head;
a rod;
a receiving part configured to pivotably receive the head and to receive the rod for connecting the rod to the shank, the receiving part comprising two legs defining a U-aped recess, each leg having a free end and an internal thread comprising a plurality of thread turns formed in one-piece with the leg;
a filling piece comprising a rod contacting surface configured to correspond with a shape of and contact an outer surface of a first portion of the rod, and a second surface opposite the rod contacting surface;
a pressure element configured to be arranged in the U-shaped recess and having a seat for receiving the rod, wherein the seat of the pressure element comprises a rod contacting surface configured to face in the direction of the filling piece for contacting a second portion of the rod, wherein a shape of the rod contacting surface of the seat is adapted to the shape of an outer surface of the second portion of the rod;
a first locking element having a central axis, a solid tubular wall around the central axis and a threaded outer surface on the solid tubular wall configured to engage with the plurality of thread turns of each leg to secure the rod in the seat, the first locking lenient also configured to contact the pressure element when assembled with the receiving part to secure the head relative to the receiving part; and
a second locking element configured to couple to the first locking element and contact the filling piece to secure the rod in the seat of the pressure element, the second locking element comprising an annular surface around the central axis configured to be facing in the direction of the rod when the rod is secured in the seat;
wherein the second surface of the filling piece is configured to contact a majority of a with of said annular surface of the second locking element when the rod is secured in the seat,
wherein the filling piece is spaced apart from the receiving part when assembled in the receiving part with the rod and the pressure element, and
wherein the second surface of the filling piece comprises a base surface opposite the rod contacting surface of the filling piece and a contact surface that projects from the base surface and away from the rod contacting surface of the filling piece to contact said annular surface of the second locking element when the filling piece and the second locking element are coupled.

15. The bone anchoring device of claim 14, wherein the annular surface of the second locking element is perpendicular to the central axis when the second locking element is coupled to the first locking element.

16. The one anchoring device of claim 14, wherein the rod is a hollow rod comprising a solid tube portion, and the receiving part is configured to receive the solid tube portion.

* * * * *

UNITED STATES PATENT AND TRADEMARK OFFICE
CERTIFICATE OF CORRECTION

| | |
|---|---|
| PATENT NO. | : 9,655,652 B2 |
| APPLICATION NO. | : 11/895364 |
| DATED | : May 23, 2017 |
| INVENTOR(S) | : Lutz Biedermann et al. |

It is certified that error appears in the above-identified patent and that said Letters Patent is hereby corrected as shown below:

In the Claims

| | |
|---|---|
| Column 6, Line 8, Claim 1 | Delete "with shape of", Insert --with a shape of-- |
| Column 6, Line 11, Claim 1 | Delete "arranged its the", Insert --arranged in the-- |
| Column 6, Line 36, Claim 1 | Delete "central ax", Insert --central axis-- |
| Column 6, Line 43, Claim 1 | Delete "part assembled", Insert --part when assembled-- |
| Column 6, Line 46, Claim 1 | Delete "flat side surfaces", Insert --flat side wall surfaces-- |
| Column 7, Line 23, Claim 9 | Delete "along direction", Insert --along a direction-- |
| Column 7, Line 27, Claim 10 | Delete "second looking element", Insert --second locking element-- |
| Column 7, Line 47, Claim 14 | Delete "U-aped", Insert --U-shaped-- |
| Column 8, Line 18, Claim 14 | Delete "locking lenient", Insert --locking element-- |

Signed and Sealed this
Twenty-fifth Day of September, 2018

Andrei Iancu
*Director of the United States Patent and Trademark Office*

CERTIFICATE OF CORRECTION (continued)
U.S. Pat. No. 9,655,652 B2

| | |
|---|---|
| Column 8, Line 29, Claim 14 | Delete "a with of said", <br> Insert --a width of said-- |
| Column 8, Line 46, Claim 16 | Delete "The one anchoring", <br> Insert --The bone anchoring-- |